United States Patent [19]

Prescher et al.

[11] Patent Number: 4,751,333
[45] Date of Patent: Jun. 14, 1988

[54] METHOD FOR THE PREPARATION OF TRIHYDROXYBENZENES

[75] Inventors: Guenter Prescher, Hanau; Gebhard Ritter, Darmstadt; Holger Sauerstein, Grosskrotzenburg, all of Fed. Rep. of Germany

[73] Assignee: Degussa Aktiengesellschaft, Frankfurt, Fed. Rep. of Germany

[21] Appl. No.: 19,092

[22] Filed: Feb. 26, 1987

[30] Foreign Application Priority Data

Mar. 11, 1986 [DE] Fed. Rep. of Germany ....... 3607924

[51] Int. Cl.$^4$ .............................................. C07C 37/60
[52] U.S. Cl. ...................................... 568/771; 568/763
[58] Field of Search ................................ 568/771, 763

[56] References Cited

U.S. PATENT DOCUMENTS

| | | | |
|---|---|---|---|
| 3,959,388 | 5/1976 | Nicolaas et al. | 568/763 |
| 4,053,523 | 10/1977 | Seifert et al. | 568/771 |
| 4,351,968 | 9/1982 | Harris | 568/771 |
| 4,387,252 | 6/1983 | Jupe et al. | 568/771 |

FOREIGN PATENT DOCUMENTS

| | | | |
|---|---|---|---|
| 122374 | 2/1984 | European Pat. Off. | 568/771 |
| 2138735 | 3/1973 | Fed. Rep. of Germany | 568/771 |
| 24056 | 6/1974 | Japan | 568/771 |
| 55-69529 | 3/1980 | Japan | 568/771 |

*Primary Examiner*—Werren B. Lone
*Attorney, Agent, or Firm*—Beveridge, DeGrandi & Weilacher

[57] ABSTRACT

Method for the conversion of resorcinol with aqueous hydrogen peroxide to obtain a mixture of 1,2,3- and 1,2,4-trihydroxybenzenes wherein the amount of water present in the initial reaction mixture is controlled to small amounts.

9 Claims, No Drawings

METHOD FOR THE PREPARATION OF TRIHYDROXYBENZENES

The present invention relates to the preparation of 1,2,3-trihydroxybenzene (pyrogallol) and 1,2,4-trihydroxybenzene (hydroxyhydroquinone).

Both of the above substances are known as strong reducing agents and have found many uses in commercial activities as follows:

Pyrogallol is used in the art of photography and lithography, in galvanizing techniques and for cosmetic preparations as well as for certain insecticides; hydroxyhydroquinone is known for use as a stabilizer, antioxidant and polymerization inhibitor and because of its reduced toxicity as compared to pyrogallol, it is also used in the cosmetic industry. See Ullmann, 4th Edition, Vol. 18, p. 223 (in German).

The most important industrial method for the preparation of pyrogallol that has been known in the art is through the decarboxylation of the naturally occurring gallic acid which occurs only in limited amounts and is itself quite expensive.

There was therefore a long standing need for a synthetic method for the preparation of pyrogallol. For almost one hundred years there have been efforts and attempts made to provide a method for obtaining pyrogallol through a conversion reaction between resorcinol and hydrogen peroxide without, however, achieving sufficient success.

For example, Wurster in the year 1887 obtained absolutely no product and only pointed out that resorcinol is very nearly almost completely decomposed through a hydrogen peroxide. (See Berichte, vol. 20, 1887, p. 2938). In 1912, H. V. Liebig described obtaining a dark brown lacquer with the formula $C_{18}H_{14}O_8$, to which he gave the name "Resorcinol Brown." He assumed that the product resulting from resorcinol, peroxide and ammonia, which produced resorcinol blue or a lacquer forming material, also resulted in a poly molecular product. See J.Pr. Vol. 2, 85, p. 258. However, in 1914, R. Hettinger founded out that the lacquer-type material was not uniform. (Biochem. Z. 65, p. 177, 1914).

Because the reaction did not lead to a definite product without a catalyst, the reaction was generally carried out in the presence of catalysts, such as for example ferrosulfate, and only the luminescence was positively determined; other properties were absent. (Z. anorg. Ch. 199, p. 400–403, 1931).

The utilization of tungstenic acid as catalyst led to the formation of maleic acid and carbon dioxide (J. Indian Chem. Soc. 19, 1942, p. 499) and in the presence of aqueous sodium hydroxide using potassium peroxydisulfate only carbon dioxide was obtained. (Atti X Congr. int. Chim. Rom, 1938, Vol. 3, p. 682 ff).

In 1963, Musso while researching auto-oxidation products of resorcinol in ammonia alkaline solutions, also carried through reactions with hydrogen peroxide, and said that condensed compounds (phenoxazone) were obtained as end products (Berichte, Vol. 96, p. 1579 ff, 1963).

Subsequenly, while investigating the kinetics of the reaction between resorcinol and hydrogen peroxide in the presence of Cu-II-ions at a pH value of 10.7 to 12.7, the authors described the end product of experiments as polymer product. It was also determined that with a pH value of only 9, the reaction proceeded extraordinarily slowly. (Inorg. Chim. Acta, Vol. 99, 1985, p. 217 ff).

The experiment involving the hydroxylation of resorcinol and hydrogen peroxide with a highly poisonous fluoroketone as catalyst led to a very limited formation of trihydroxybenzenes; however, at least 90% of the reacted hydrogen peroxide, in spite of the use of this catalyst, did not convert to the desired products. (JP-PS No. 50-151-832, 1975).

In accordance with these various developments and research which took place between 1887 and 1985 concerning the reaction between resorcinol and hydrogen peroxide, it was therefore to be expected that experts in the art would assume that there existed a large number of products, for the most part without a specifically determined composition and that these synthetic methods would not be suitable for the preparation, especially in commercial amounts, of pyrogallol and hydroxyhydroquinone.

The experts in the art therefore went off in a totally different direction in order to prepare pyrogallol, for example, through heating of specific diaminophenols under acidic conditions (DE-OS No. 24 45 336); through dealkylation of pyrogallol ethers which are expensive because of multiple halogenated aromatic ethers, (DE-OS No. 26 27 874); through use of tetrahalogen derivatives of cyclohexanone and their basic catalyzed hydrolysates (DE-OS No. 26 53 446). Also the oxidation of a mono- or divalent aromatic hydroxyaldehyde, specially prepared therefor, under basic reaction conditions using for example hydrogen peroxide, has been described (European Pat. No. 00 25 659).

In spite of the requirement of these generally multi-step methods, the yields obtained of pyrogallol and hydroxyhydroquinone leave much to be desired and none of these methods of preparation were commercially feasible for the preparation of both materials.

It is therefore an object of the present invention to provide a method for synthesizing pyrogallol and hydroxyhydroquinone, without loss, through oxidation of resorcinol with hydrogen peroxide.

It has been determined that the object of the present invention can be obtained by carrying out a process wherein resorcinol is contacted with aqueous hydrogen peroxide at a temperature of at least 60° C. when the initial amount of water in the mixture before initiation of the reaction ranges between 0.1 to 36 weight percent, based on the total weight of the mixture.

It is particularly desirable to contact the resorcinol at a temperature of at least 80° C. with the aqueous hydrogen peroxide. Spontaneously increasing temperatures up to 150° C. can be utilized from the commencement of the reaction. If higher temperatures are desired, it is necessary to heat the reaction. A particularly suitable temperature range for initiation of the reaction and for bringing into contact the resorcinol and aqueous hydrogen peroxide is in the range of 110° to 120° C.

When utilizing higher temperatures in accordance with the process of the present invention, it has been found that the conversion is favored in the direction of forming trihydroxybenzenes. However, the quantities of water that are introduced before the beginning of the reaction also have an influence on the reaction.

Preferably, the amounts of water that are introduced before the reaction range between 0.5 to 15 weight percent, based on the mixture of the resorcinol and hydrogen peroxide, and particularly advantageous are amounts of water of between 0.8 and 10 weight percent, and especially between 0.8 and 6 weight percent.

The introduction of molten resorcinol has been found to be particularly desirable. Also, in the indicated temperature range, saturated aqueous solutions of resorcinol, for example, saturated at 80° to 100° C. can be suitably used in accordance with the present invention. The reaction times increase in general with increasing water content which is shown, for example, in Examples 2 and 6 hereinafter.

The yields are also influenced by the water content of the initial starting reaction. This influence or effect, however, does not occur markedly with the introduction of a melt of resorcinol, see Examples 2 to 4. However, it does occur with the utilization of a saturated solution to distinctly direct the reaction in the direction whereby a reduction in the yield is obtained, see Examples 6 and 7.

In these described situations, exactly the same molar ratio of resorcinol to hydrogen peroxide (100% concentration) is introduced; namely 10:1. This relationship ranges under normal conditions between 5 to 20:1; preferably a ratio of 10 to 20:1. However, because with a mole ratio of 10:1 very good properties are obtained, for a commercial or industrial utilization this molar ratio is to be preferred in that case the amount of the unconverted resorcinol is not unnecessarily large.

Aqueous hydrogen peroxide is introduced in conventional solutions of from 20 to 85 weight percent hydrogen peroxide, preferably between 30 to 85 weight percent.

Through the method of the present invention it was for the first time possible to carry out a direct reaction; that is, without utilization of a catalyst, by reacting resorcinol and aqueous hydrogen peroxide to obtain 1,2,3- and 1,2,4-trihydroxybenzene and indeed with even very good yields, solely through utilization of higher temperatures and a controlled limited amount of water at the beginning of the reaction. A development of this nature was not to be expected in the light of the disappointments that had occurred in accordance with the level of technology over the last hundred years.

The following examples are intended to further illustrate the invention. As may be seen from the examples, the distinct influence of the temperature and the initial water content on the reaction is clearly ascertainable.

EXAMPLE 1

110 g (1.0 mole) resorcinol were warmed to 100° C. To this melt there was added with stirring 2.52 g (0.05 mole) 70% hydrogen peroxide. The temperature in the reaction solution increases thereafter to about 133° C. After subsidence of the exothermic reaction after 10 minutes, there was determined to be a hydrogen peroxide conversion of 97.8%. The reaction mixture contained 5.5 g 1,2,4-trihydroxybenzene and 0.85 g pyrogallol, which corresponds to a total yield of trihydroxybenzenes of 99.2%, based on the converted hydrogen peroxide.

The ratio of hydroxyhydroquinone to pyrogallol was 6.4:1.

EXAMPLE 2

55 g (0.5 mole) resorcinol were heated to 110° C. There was added to this melt 2.43 g (0.05 mole) 70% hydrogen peroxide solution with stirring. The temperature of this reaction solution thereby increases up to 162° C. After subsidence of the exothermic reaction after 10 minutes a hydrogen peroxide conversion of 99.8% is determined. The reaction mixture then contains 4.8 g 1,2,4-trihydroxybenzene and 0.95 g pyrogallol, which corresponds to a total yield of trihydroxybenzenes of 91.1%, based on the converted hydrogen peroxide.

The ratio of hydroxyhydroquinone to pyrogallol was 5.0:1.

EXAMPLE 3

55 g (0.5 mole) resorcinol are heated up to 110° C. To the stirred melt, there is added 2 g (0.05 mole) 85% hydrogen peroxide. The temperature in the reaction solution rises thereafter to 135° C. After subsidence of the exothermic reaction, after 10 minutes there is determined to be a 98% conversion of the hydrogen peroxide. The reaction mixture contains then 4.65 g 1,2,4-trihydroxybenzene and 1.1 g pyrogallol, which corresponds to a total yield of trihydroxybenzenes of 93%, based on the conversion of the hydrogen peroxide.

The ratio of hydroxyhydroquinone to pyrogallol is 4.2:1.

EXAMPLE 4

55 g (0.5 mole) resorcinol are heated to 110° C. To this stirred melt, there is added 5.7 g (0.05 mole) 30% hydrogen peroxide. The temperature in the reaction solution increases up to 137° C. After subsidence of the exothermic reaction, after 10 minutes the conversion of hydrogen peroxide is determined to be 99%. The reaction mixture contains 4.68 g 1,2,4-trihydroxybenzene and 1.35 g pyrogallol, which corresponds to a total yield of trihydroxybenzenes of 96%, based on the conversion of hydrogen peroxide.

The ratio of hydroxyhydroquinone to pyrogallol is 3.4:1.

EXAMPLE 5

55 g (0.5 mole) resorcinol are heated up to 110° C. in a nitrogen atmosphere. To this stirred melt there is then added 4.86 g (0.1 mole) 70% hydrogen peroxide. The temperature in the reaction solution increases thereafter up to 175° C. After 10 minutes the hydrogen peroxide conversion was determined to be 100%. The reaction mixture then contains 7.93 g 1,2,4-trihydroxybenzene and 2.52 g pyrogallol, which corresponds to a total yield of trihydroxybenzenes of 83%, based upon the introduced hydrogen peroxide.

The ratio of hydroxyhydroquinone to pyrogallol was 3.1:1.

EXAMPLE 6

55 g (0.5 mole) resorcinol were heated to 100° C. and mixed with 6 g water. To this saturated solution there is then added 2.52 g (0.05 mole) 70% hydrogen peroxide with vigorous stirring. The temperature in the reaction solution then rises to about 112° C. After 20 minutes there was determined to be hydrogen peroxide conversion of 100%. The reaction mixture then contains 3.54 g 1,2,4-trihydroxybenzene and 1.06 g pyrogallol which corresponds to a total yield of 70.3% based on the hydrogen peroxide that is introduced into the reaction.

The ratio of hydroxyhydroquinone to pyrogallol is 3.3:1.

EXAMPLE 7

55 g (0.5 mole) resorcinol were heated to 100° C. and treated with 6 g water. To this saturated solution of resorcinol and water there is added 5.67 g (0.05 mole) 30% hydrogen peroxide with vigorous stirring. The temperature in the solution then rises up to 106° C. After 20 minutes the conversion of the hydrogen peroxide was determined to be 100%. The reaction mixture then contains 2.7 g 1,2,4-trihydroxybenzene and 1.55 g 1,2,3-trihydroxybenzene, which corresponds to a total yield of trihydroxysenzens of 66.8% based on the hydrogen peroxide introduced into the reaction.

The ratio of hydroxyhydroquinone to pyrogallol is 1.74:1.

EXAMPLE 8

11 g (0.1 mole) resorcinol were dissolved in 20 g water at 30° C. and then treated with 4.86 g (0.1 mole) 70% hydrogen peroxide. After 3 hours of reaction time at 30° C., the hydrogen peroxide conversion was determined to be 60% whereby however there was not found to be any observable amount of trihydroxybenzenes. After this time, the temperature was raised to 80° C. After 1 hour of reaction time, the hydrogen peroxide is then completely converted and whereby a limited amount of trihydroxybenzenes on the order of less than 10% were found to be formed.

EXAMPLE 9

11 g (0.1 mole) resorcinol were dissolved in 20 g water at 80° C. and then treated with 4.86 g (0.1 mole) 70% hydrogen peroxide. During the heating phase there was observed to be a brown coloration. The temperature in the reaction solution rose thereafter to 90° C. After 10 minutes, a hydrogen peroxide conversion of 100% was determined. The reaction mixture contained at most limited amounts of less than 10% of trihydroxybenzenes.

EXAMPLE 10

55 g (0.5 mole) resorcinol were heated up to 80° C. and then dissolved with 8 g water in solution. To this saturated solution there was then introduced 2.43 g (0.05 mole) 70% hydrogen peroxide with vigorous stirring. The temperature did not rise during this total conversion. After 20 or 60 minutes, a hydrogen peroxide conversion of 92.9 or 100% was determined. The reaction mixture contains then 4.33 g 1,2,4-trihydroxybenzene and 1.0 g 1,2,3-trihydroxybenzene, which corresponds to a total yield of trihydroxybenzenes of 84% based on the introduced hydrogen peroxide.

EXAMPLE 11

55 g (0.5 mole) resorcinol were heated to 60° C. and then treated with 13 g water. To this saturated solution there is added 2.43 g (0.05 mole) 70% hydrogen peroxide with vigorous stirring. The temperature of the reaction solution did not increase during this addition. After a total of 4 hours the hydrogen peroxide conversion was determined to be 98.2%. The reaction mixture then contained 2.26 g 1,2,4-trihydroxybenzene and 0.6 g 1,2,3-trihydroxybenzene, which corresponds to a total yield of trihydroxybenzene of 45% based on the total introduced hydrogen peroxide.

Further variations and modifications of the above-described invention will be apparent to those skilled in the art based on the foregoing and are intended to be encompassed by the claims appended hereto.

The German priority application No. P 36 07 924.3 is relied on and incorporated herein by reference.

We claim:

1. A method for the preparation of 1,2,3-and 1,2,4-trihydroxybenzenes by hydroxylation of resorcinol with hydrogen peroxide comprising
    contacting the resorcinol with aqueous hydrogen peroxide at a temperature of at least 60° C.,
    and reacting resorcinol with the hydrogen peroxide for a sufficient time to produce the said trihydroxybenzenes, and
    wherein the initial amount of water in the aqueous mixture of resorcinol and hydrogen peroxide ranges from 0.1 to 36 weight percent based on the total mixture.

2. The method in accordance with claim 1, wherein the temperature is at least 80° C.

3. The method in accordance with claim 1, wherein the temperature is from 110° to 120° C.

4. The method in accordance with claim 1., wherein the resorcinol is in the form of a melt.

5. The method in accordance with claim 1, wherein the amount of water present in the reaction system is 0.5 to 15 weight percent based on the weight of the resorcinol and hydrogen peroxide.

6. The method in accordance with claim 1, wherein the amount of water in the reaction system is 0.8 to 10 weight percent based on the weight of the resorcinol and the hydrogen peroxide.

7. The method in accordance with claim 1, wherein the amount of water present in the reaction system is 0.8 to 6 weight percent based on the total of the resorcinol and hydrogen peroxide.

8. The method in accordance with claim 1, wherein the reaction is carried out in the absence of a catalyst.

9. The method of claim 1, wherein the reaction is carried with stirring.

* * * * *